United States Patent
Litzenberger

(10) Patent No.: US 12,376,810 B1
(45) Date of Patent: Aug. 5, 2025

(54) ARTICULATING ARM FOR PORTABLE C-ARM

(71) Applicant: CARESTREAM HEALTH, INC., Rochester, NY (US)

(72) Inventor: Michael A. Litzenberger, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 294 days.

(21) Appl. No.: 18/192,169

(22) Filed: Mar. 29, 2023

Related U.S. Application Data

(60) Provisional application No. 63/327,006, filed on Apr. 4, 2022, provisional application No. 63/327,011, filed
(Continued)

(51) Int. Cl.
*A61B 6/00* (2024.01)

(52) U.S. Cl.
CPC .......... *A61B 6/4405* (2013.01); *A61B 6/4441* (2013.01)

(58) Field of Classification Search
CPC .... A61B 6/40; A61B 6/42; A61B 6/56; A61B 6/4441; A61B 6/4405; A61B 6/5235; A61B 6/466; A61B 34/20; A61B 34/30; A61B 90/39; A61B 6/463; A61B 90/50; A61B 90/36; A61B 6/505; A61B 34/10; A61B 2090/372; A61B 2090/376; A61B 2090/3937; A61B 2034/105; A61B 2090/367; A61B 6/12; A61B 6/032; A61B 90/90; A61B 2034/2059; A61B 2090/3966; A61B 2034/2055; A61B 17/1757; A61B 90/96; A61B 2090/365; A61B 17/1703; A61B 2034/2051; A61B 2090/502; A61B 34/25; A61B 2034/302; A61B 2090/371; A61B 2034/2065; A61B 2034/301; A61B 2090/373; A61B 2090/3995; A61B 2090/3983; A61B 2090/364; A61B 90/98; A61B 2090/363; A61B 2034/107; A61B 2090/061; A61B 2034/303; A61B 8/4416; A61B 6/5264; A61B 6/5258; A61B 46/20; A61B 46/00; A61B 6/5223; A61B 6/5247; A61B 6/583; A61B 6/5241; A61B 6/584; A61B 2090/395; A61B 6/587; A61B 6/4452; A61B 6/588; A61B 6/547; A61B 2562/0223; A61B 6/46; A61B 6/54; A61B 6/566; A61B 6/548; A61B 6/461;
(Continued)

(56) References Cited

U.S. PATENT DOCUMENTS

| | | | |
|---|---|---|---|
| 4,768,216 A * | 8/1988 | Harvey | H05G 1/265 378/112 |
| 6,609,826 B1 * | 8/2003 | Fujii | A61B 6/56 378/197 |

(Continued)

*Primary Examiner* — Irakli Kiknadze

(57) ABSTRACT

A mobile C-arm radiographic imaging system provides a rigid C shaped support arm for securing an x-ray source and an x-ray detector in a fixed spatial relationship relative to each other. A mobile base supports the rigid support arm using an articulating segmented arm attached to the base and to the rigid support arm. The articulating arm comprises three pivot mechanisms configured to manually translate the support arm relative to the base and to manually rotate the support arm relative to the base about any one or more of three different vertical axes.

14 Claims, 1 Drawing Sheet

Related U.S. Application Data on Apr. 4, 2022, provisional application No. 63/327,016, filed on Apr. 4, 2022.

(58) Field of Classification Search
CPC ..... A61B 6/4266; A61B 6/4494; A61B 6/467; A61B 6/4476; A61B 6/542; A61B 6/4208; A61B 6/44; A61B 6/4283; A61B 6/4464; A61B 6/545; A61B 6/563; A61B 6/465; A61B 6/4233; A61B 6/025; A61B 6/107; A61B 6/5211; A61B 6/487; A61B 6/4458; A61B 6/482; A61B 6/4007; A61B 6/468; A61B 6/5205; A61B 6/488; A61B 6/541; A61B 6/50; A61B 6/4085; A61B 6/035; A61B 6/4482; A61B 6/4429; A61B 6/04; A61B 6/527; A61B 6/4447; A61B 6/0492; H01M 50/247; H01M 50/20; H01M 4/5825; H01M 10/0525; G06T 7/73; G06T 7/33; G06T 2207/10081; G06T 2207/10072; G06T 2200/32; G06T 2207/10088; G06T 2207/30012; G06T 2207/10116; G06T 15/08; G06T 15/06; G06T 2207/10124; G06T 7/30; G06N 20/00; G01N 23/04; G16H 50/20; H04W 4/70; H05G 1/02; H01J 35/10; H01J 35/06
USPC .......................................................... 378/198
See application file for complete search history.

(56) References Cited

U.S. PATENT DOCUMENTS

| | | | |
|---|---|---|---|
| 2002/0085681 A1* | 7/2002 | Jensen | A61B 6/463 378/197 |
| 2008/0122936 A1* | 5/2008 | Lomnes | A61B 6/08 348/E5.025 |
| 2014/0098930 A1* | 4/2014 | Litzenberger | A61B 6/025 378/4 |
| 2014/0233702 A1* | 8/2014 | Suzuki | A61B 6/42 378/198 |

* cited by examiner

ARTICULATING ARM FOR PORTABLE C-ARM

CROSS REFERENCE TO RELATED APPLICATIONS

This application claims priority to U.S. Patent Application Ser. No. 63/327,006, filed Apr. 4, 2022, in the name of Zacks et al., and entitled ARTICULATING ARM FOR PORTABLE C-ARM WITH ATTACHABLE MONITOR CART; U.S. Patent Application Ser. No. 63/327,011, filed Apr. 4, 2022, in the name of Zacks et al., and entitled INTERCHANGEABLE DETECTORS ON PORTABLE C-ARM AND WORKING AREA LIGHTING; and U.S. Patent Application Ser. No. 63/327,016, filed Apr. 4, 2022, in the name of Zacks et al., and entitled C-ARM SYSTEM, all of which are hereby incorporated by reference herein in their entirety.

BACKGROUND OF THE INVENTION

The subject matter disclosed herein relates to mobile C-arm x-ray systems.

Currently, mobile C-arm radiographic imaging systems utilize several types of structures to support and enable the imaging structure (C-shaped arm, detector, and radiation source) to move horizontally. The most common arrangement of support structure is a horizontally translating boom that primarily travels in a direction perpendicular to the front of a mobile cart. The boom may be connected to a rotating element, which has a limited amount of rotational travel to keep the center of mass of the imaging structure within a designated range to ensure stability of the apparatus. The rotating element, in turn, is connected to the mobile C-arm cart. In this arrangement, the imaging structure may be translated horizontally and rotated about a vertical axis at the same time, to enable an imaging region between the source and detector to be selectively moved. This motion changes the orientation of the source and detector with respect to the patient.

The discussion above is merely provided for general background information and is not intended to be used as an aid in determining the scope of the claimed subject matter.

BRIEF DESCRIPTION OF THE INVENTION

A mobile C-arm radiographic imaging system provides a rigid C shaped support arm for securing an x-ray source and an x-ray detector in a fixed spatial relationship relative to each other. A mobile base supports the rigid support arm using an articulating segmented arm attached to the base and to the rigid support arm. The articulating arm comprises three pivot mechanisms configured to manually translate the support arm relative to the base and to manually rotate the support arm relative to the base about any one or more of three different vertical axes. An advantage that may be realized in the practice of some disclosed embodiments of the mobile C-arm radiographic imaging system is easier maneuverability and positioning.

In one embodiment, a mobile C-arm radiographic imaging system includes a C shaped arm supported by a base cart. An articulating assembly is attached to the base cart and to the C shaped arm. The articulating assembly enables the C shaped arm to be manually moved, relative to the base cart, in various directions along a first plane. The articulating assembly has three pivot mechanisms and three rigid arms each attached to at least one of the pivot mechanisms. The three pivot mechanisms each comprise a rotational axis perpendicular to the first plane, and are each configured to enable at least one of the rigid arms attached thereto to rotate about its rotational axis.

In one embodiment, a mobile C-arm radiographic imaging system includes a rigid support arm for securing an x-ray source and an x-ray detector in a fixed spatial relationship relative to each other, and a base for supporting the rigid support arm. The base includes an articulating arm attached to the base and to the rigid support arm. The articulating arm has three pivot mechanisms configured to manually translate the support arm along a horizontal plane relative to the base and to manually rotate the support arm relative to the base about any one or more of three different vertical axes.

In one embodiment, three rotatable arms are supported by three pivot joints. The combination of these arms and joints allows the imaging support structure to articulate and be moved horizontally to any position within the limits of the length of the arms and rotation limits of the pivots. The orientation of the detector may be left unchanged during this movement. The rotatable arms may be held in position by one or more brakes. Releasing the brake(s) enables the arms to articulate in any horizontal direction. If more than one brake is present, one or more braking elements can be released to allow movement of one or more arms. The support structure may include synchronous elements to rotatably limit any of the rotatable arms about a corresponding vertical axis. Thus, a subset of rotatable arms may be rotationally limited with respect to the cart.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
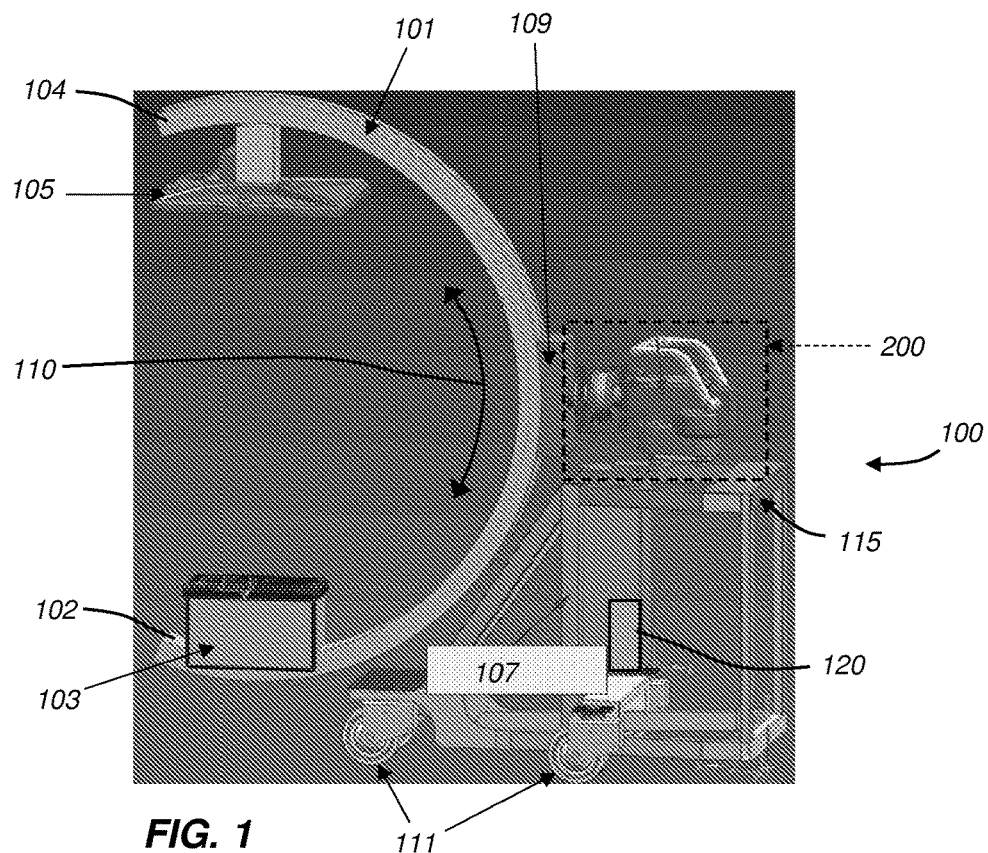
FIG. 1 is a perspective view of an exemplary mobile C-arm imaging system.

FIG. 1 is a perspective view of a mobile C-arm x-ray system 100, which includes a rigid, arc shaped support arm 101 having a first end 102 with an x-ray source assembly 103 affixed thereto, and a second end 104 having a digital radiographic (DR) detector 105 affixed thereto. The x-ray source assembly 103 is fixed in a position to emit an x-ray beam toward the DR detector 105. The x-ray source assembly 103 may include a collimator to control a size and shape of the emitted x-ray beam. A patient positioned between the x-ray source assembly 103 and the DR detector 105 may be exposed to an x-ray beam emitted by the x-ray source assembly 103, and a radiographic image of the patient may be captured in the DR detector 105. Such a patient is typically lying on a patient bed that is configured to be positioned between the x-ray source assembly 103 and the DR detector 105. The support arm 101 is attached to a mobile cart 107 using a driver 109 and an articulating arm 200. The driver 109 may be motorized and configured to translate the support arm 101 relative to the driver 109 along both directions indicated by the arrow 110. The driver 109 may be used for moving and positioning the source assembly 103 and detector 105, as desired. Wheels 111 attached to a bottom side of the mobile cart 107 and a handle bar 115 are provided for an operator to manually, rollably push and pull the mobile C-arm x-ray system 100 to any location as desired. A control system 120 may include a processing system in electrical and digital communication with the x-ray source assembly 103 and the DR detector 105 for controlling exposure procedures using the mobile C-arm x-ray system 100. The control system 120 may be used to initiate and control firing of the x-ray source assembly 103 in synchrony with an image capture phase of the detector 105, for example. Electronic memory in control system 120 may be used to digitally communicate with the DR detector 105 to receive digital radiographic images captured by, and transmitted from, the DR detector 105.

Figure 2:
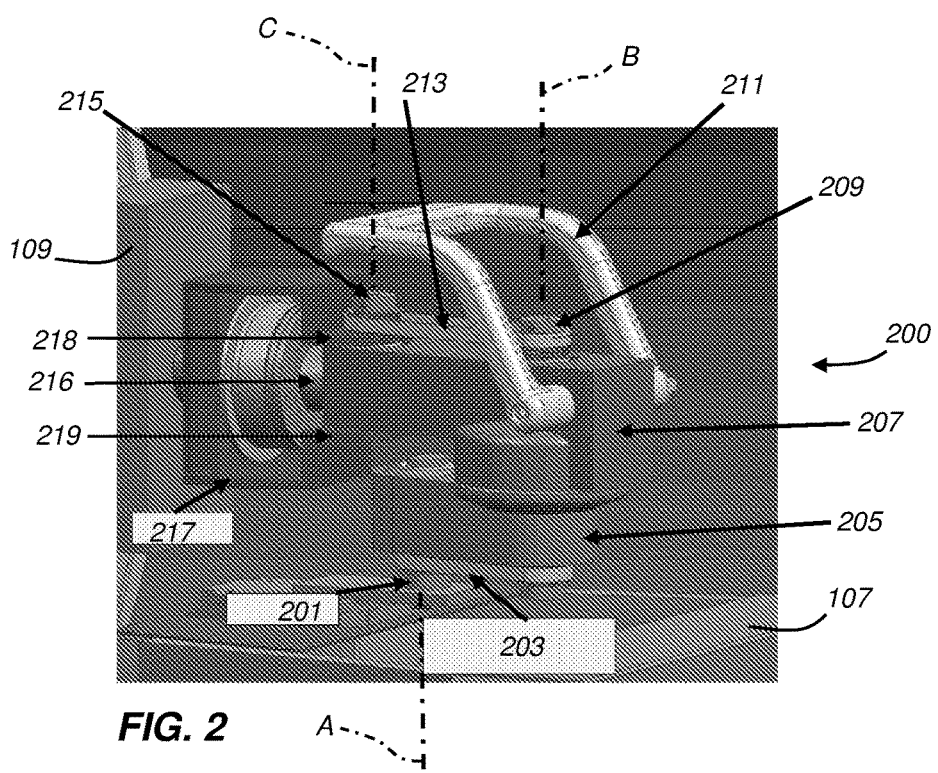
FIG. 2 is a perspective view of an exemplary articulating arm.

FIG. 2 is a perspective view of articulating arm 200 which connects the mobile cart 107 to the arc shaped support arm 101 via driver 109. Articulating arm 200 includes three rigid, rotatable segments each corresponding to a different one of three rotational axes. The first rigid segment 205 is connected to the mobile cart 107 by a bolt 201 extending therethrough. The bolt 201 is aligned coaxially with a first vertical rotational axis A, to allow the first rigid segment 205 to rotate about vertical rotational axis A relative to the mobile cart 107. The second rigid segment 207 is connected to the first rigid segment 205 by a bolt 209 extending therethrough. The bolt 209 is aligned coaxially with a second rotational axis B, to allow the second rigid segment 207 to rotate about vertical rotational axis B relative to the first rigid segment 205. The third rigid segment 217 is connected to the second rigid segment 207 by a bolt 215 extending therethrough. The bolt 215 is aligned coaxially with a third vertical rotational axis C, to allow the third rigid segment 217 to rotate about rotational axis C relative to the second rigid segment 207. The third rigid segment 217 is formed in the shape of a C having a top flange 218 secured to a top side of rigid segment 207 and a bottom flange 219 secured to a bottom side of rigid segment 207; both the top and bottom flanges are secured to rigid segment 207 using bolt 215 extending therethrough. The third rigid segment 217 is fixed to the driver 109 by a bolt 216 extending therethrough. In one alternative embodiment, the distance between rotational axes B and C may be configured to be greater than the distance between rotational axes A and B. Hence, in this embodiment, axes A and C cannot coincide by manipulating rigid segments 205, 207, and 217.

In one alternative embodiment, synchronous elements 203 and 213 may be attached to the articulating arm 200 to limit angular rotation of rigid segments 205, 207, and 217 by providing a limiting detent mechanism against bolts 201, 209, 215, respectively. In addition, a brake mechanism within second rigid segment 207 may be activated by pivoting a manual lever 211, attached thereto, that locks in place and prevents relative rotation of second rigid element 207 about either one or both of rotational axes B (first rigid segment 205 rotation relative to second rigid segment 207) and C (third rigid segment 217 rotation relative to second rigid segment 207).

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A mobile C-arm radiographic imaging system comprising:
   a C shaped arm;
   a base for supporting the C shaped arm; and
   an articulating assembly attached to the base and to the C shaped arm, the articulating assembly configured to enable the C shaped arm to be manually moved, relative to the base, in various directions along a first plane;
   the articulating assembly comprising:
      three pivot mechanisms having three separate rotational axes all simultaneously perpendicular to the first plane;
      three rigid arms each attached to at least one of the pivot mechanisms,
      wherein the three pivot mechanisms each comprise only one of the three separate rotational axes perpendicular to the first plane, and wherein the three pivot mechanisms are each configured to enable only one of the rigid arms attached thereto to rotate about a corresponding one of the three separate rotational axes.

2. The system of claim 1, further comprising at least one brake configured to prevent at least one of the rigid arms from rotating about a corresponding one of the three separate rotational axes.

3. The system of claim 2, further comprising at least one synchronous element configured to limit rotational movement of one of the rigid arms about a corresponding one of the three separate rotational axes.

4. The system of claim 3, wherein the base comprises wheels for rollably transporting the mobile C-arm radiographic imaging system.

5. The system of claim 1, wherein the three separate rotational axes are configured to prevent a coaxial alignment between any two of the three separate rotational axes.

6. A mobile radiographic imaging system comprising:
   a rigid support arm for securing an x-ray source and an x-ray detector in a fixed spatial relationship relative to each other; and
   a base for supporting the rigid support arm, the base comprising an articulating arm attached to the base and to the rigid support arm,
   wherein the articulating arm comprises three pivot mechanisms each fixed to rotate only horizontally about one of three different vertical axes and configured to manually translate the rigid support arm, relative to the base, along a horizontal plane by rotating any one or more of the three pivot mechanisms, wherein the three pivot mechanisms are each configured to rotate about only one of the three different vertical axes.

7. The system of claim 6, wherein the three different vertical axes are configured to prevent a coaxial alignment between any two of the three different vertical axes.

8. The system of claim 6, further comprising at least one brake configured to prevent at least one of the pivot mechanisms from rotating about a corresponding vertical axis.

9. The system of claim 6, further comprising at least one synchronous element configured to limit rotational movement of at least one of the pivot mechanisms about a corresponding vertical axis.

10. A mobile radiographic imaging system comprising:
    a rigid support arm for securing an x-ray source and an x-ray detector in a fixed spatial relationship relative to each other, wherein the x-ray source and the x-ray detector are sufficiently spaced to allow a patient to be positioned therebetween; and
    a base for supporting the rigid support arm, the base comprising an articulating arm attached to the base and to the rigid support arm,
    the articulating arm comprising three rotational axes all simultaneously positioned in a parallel vertical orientation, wherein the articulating arm is configured to manually translate the rigid support arm horizontally, the articulating arm further comprising three rigid segments configured to each be separately rotatable about one of the three parallel vertical axes.

11. The system of claim 10, wherein the three rigid segments each comprise a pivot mechanism configured to allow manual rotation of a corresponding rigid segment about one of the three parallel vertical axes.

12. The system of claim 11, further comprising at least one brake configured to prevent at least one of the pivot mechanisms from rotating about a corresponding vertical axis.

13. The system of claim 11, further comprising at least one synchronous element configured to limit rotational movement of at least one of the pivot mechanisms about a corresponding vertical axis.

14. The system of claim 10, wherein the three parallel vertical axes are configured to prevent a coaxial alignment between any two of the three parallel vertical axes.

* * * * *